United States Patent [19]

Fleming et al.

[11] Patent Number: 5,476,010
[45] Date of Patent: Dec. 19, 1995

[54] HANDS-FREE ULTRASONIC TEST VIEW (HF-UTV)

[75] Inventors: Marvin F. Fleming, Los Altos; Samuel Hersh, Danville, both of Calif.

[73] Assignee: Sierra Matrix, Inc., Fremont, Calif.

[21] Appl. No.: 357,972

[22] Filed: Dec. 14, 1994

Related U.S. Application Data

[63] Continuation of Ser. No. 913,462, Jul. 14, 1992, abandoned.
[51] Int. Cl.$^6$ .......................... G01N 29/10; G01N 29/22
[52] U.S. Cl. .......................... 73/620; 73/629; 73/633; 340/980
[58] Field of Search .................... 73/579, 620, 866.3, 73/627, 629, 633; 340/705, 825.1, 825.11, 825.12, 825.13, 825.14, 825.15, 980

[56] References Cited

U.S. PATENT DOCUMENTS

| | | | |
|---|---|---|---|
| 4,193,306 | 3/1980 | Flaherty et al. | 73/629 |
| 4,622,517 | 11/1986 | Arnaud et al. | 73/633 |
| 4,757,714 | 7/1988 | Pardy et al. | 73/597 |
| 5,003,300 | 3/1991 | Wells | 340/705 |
| 5,166,778 | 11/1992 | Beamon, III | 340/705 |

OTHER PUBLICATIONS

J. P. Crhlesworth, *Engineering Applications of Ultrasonic Time-of-Fligh Diffraction*, Research Studies Press, pp. 14–15.

L. J. Busse et al., *Review and Discussion of the Development of Synthetic Aperture Focusing Technique for Ultrasonic Testing (SAFT–UT*, pp. 11–16.

J. J. Thomsen et al., Quality Control of Composite Materials by Neural Network Analysis of Ultrasonic Power Spectra, *Materials Evaluation*, May 1991, pp. 594–600.

Ultra Image III, An Integrity Assurance System, *SAIC Ultra Image International*.

Acoustic Crack Detector (ACD), *Bridge Inspection System, Maintenance Manual*, Federal Highway Administration, Jan. 1975, pp. 1–3.

Automated Imaging System or Bridge Inspection, *U.S. Department of Transporation, Federal Highway Administration*, Final Report, Mar. 1988, pp. 5–7.

EPOCH, Digital Accuracy, Digital Simplicity, *Panametrics*.

P–Scan, Projection Image Scanning, *Force Institutes*.

Dupont NDT Instruments Ultrasonic OFT–1 and OFT–2.

Zoom Ultrasonic Scanning, Data Acquisition, & Image Processing, Transacan 5.0.

TestPro, Infometrics.

ALARA II, VCR, *The Virginia Corporation of Richmond*.

Sonotek, *Sonix*.

Intraspect Family of Ultrasonic and Eddy Current Imaging Systems, *ABB AMDATA, Inc*.

Ultrasonic Thickness Gaging plus Waveform Verification, 26 DL Plus, *Panametrics, Inc*.

(List continued on next page.)

*Primary Examiner*—Hezron E. Williams
*Assistant Examiner*—Rose M. Finley
*Attorney, Agent, or Firm*—Allston L. Jones

[57] ABSTRACT

A self-contained, portable, hands free, one man ultrasonic test view is disclosed. The system can include a variety of features including a semiautomatic scanner for positioning a probe at various locations within a selected region of a specimen that is powered only in one axis with the second axis being manually advanceable by the user. A second feature is a display that is mountable in front of one eye so that the user of the system can simultaneously view the displayed ultrasonic response signal with one eye while viewing the specimen with the other eye to mentally superimpose the one on the other. Another feature is the inclusion in the processor of a voice recognition device to detect and translate voice commands to select and control the operations of the processor together with a microphone for the user to deliver voice commands to the system. Yet another feature is the inclusion in the processor of memory devices capable of storing the returned and corresponding processed signals and the system set-up parameters for later use. There is also a battery power subsystem to make the system fully portable.

6 Claims, 16 Drawing Sheets

OTHER PUBLICATIONS

Krautkramer Branson.
New USK7D, Portable Flaw Detector with Digital Control and Memory, *Krautkramer Branson*.
USD10, Portable Digital Ultrasonic Flaw Detector for Precise Evaluation and Documentation, *Krautkramer Branson*.
Sonatest Flaw Detectors.
NDT International, Inc.
Digital Ultrasonic Inspection System, *Tecrad*.
Ultrasonic Sciences.
Spectra Scan Software Programs, *California Data Corporation*.
EPOC II, *Panametrics, Inc.*
UDRPS–2, *Dynacon*.

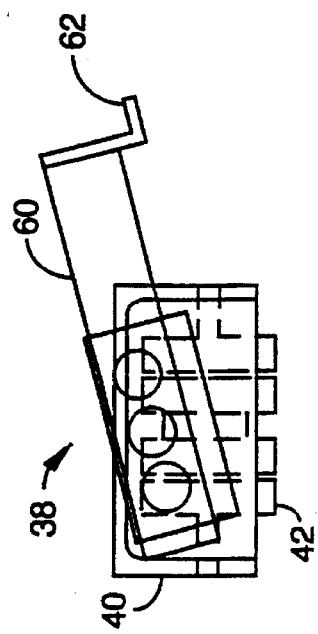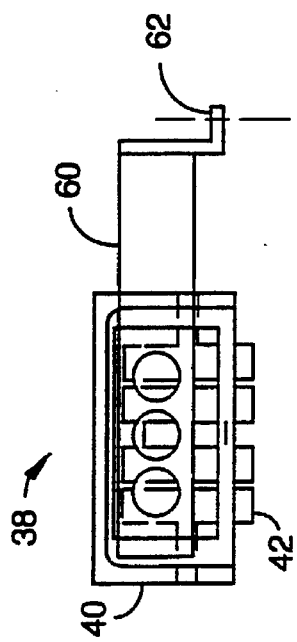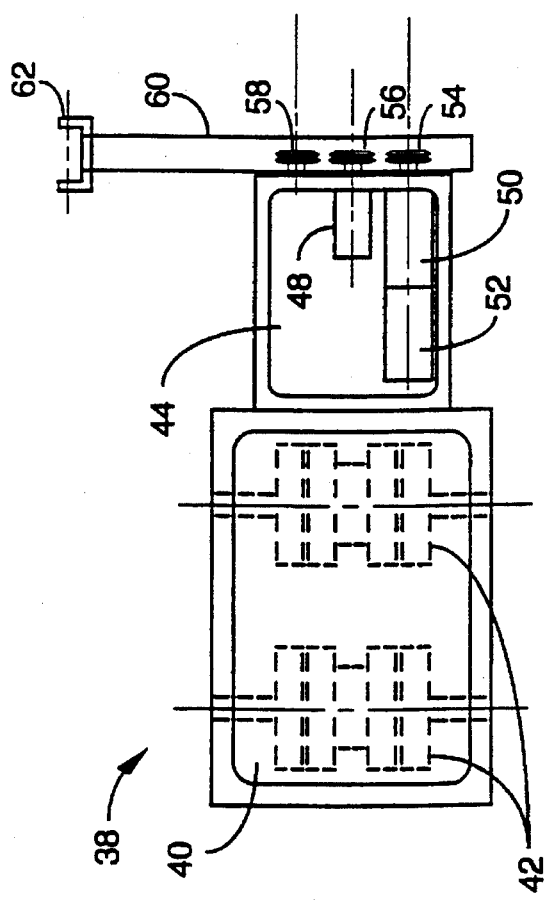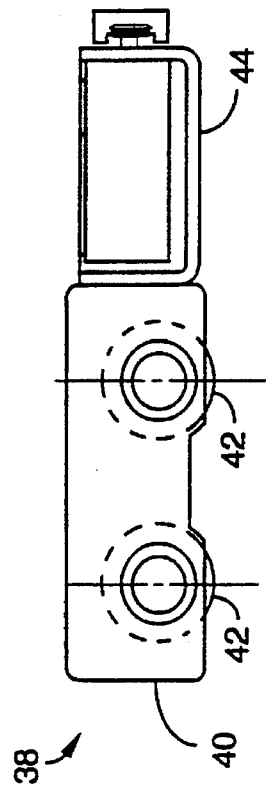

| Spoken Word | Mouse | Key | Scroll Function | Other Function |
|---|---|---|---|---|
| Up | ← | Up arrow | Up | Select menu, list item above |
| Down | → | Down arrow | Down | Select menu, list item above |
| Left | ↓ | Left arrow | Left | Select menu to left, move insertion point left |
| Right | ↑ | Right arrow | Right | Select menu to right, move insertion point right |
| OK | | Enter | | Do selected command |
| Cancel | | Esc | | Cancel a selection |
| Enter | | Enter | | Choose selected command |
| Tab | | Tab | | Move to next option |
| Shift Tab | | Shift+Tab | | Move to previous option |
| Backspace | | | | Delete text to left of insertion point |
| Spacebar | | | | Toggles check box on or off |
| Shift | | Shift | | Selects shifted functions |
| Alt | | Alt | | Activate menu bar |
| Control | | Ctrl | | Selects control functions |
| Home | Drag thumb far left | Home | Far left | |
| End | Drag thumb far right | End | Far right | |
| Control Home | Drag to top | Ctrl+Home | Beginning of topic | |
| Control End | Drag to bottom | Ctrl+End | End of topic | |
| Page Up | Click above thumb | PgUp | Up 1 window | Scrolls up through list several items at a time |
| Page Down | Click below thumb | PgDn | Down 1 window | Scrolls down through list several items at a time |
| Control Page Up | Click left of thumb | Ctrl+Page Up | Left 1 window | |
| Control Page Down | Click right of thumb | Ctrl+Page Down | Right 1 window | |

FIGURE 16

HANDS-FREE ULTRASONIC TEST VIEW (HF-UTV)

This is a continuation of application of Ser. No. 07/913,462 filed on Jul. 14, 1992, now abandoned.

FIELD OF THE INVENTION

This invention relates to a portable ultrasonic inspection apparatus for performing nondestructive testing of engineered materials and structures, a few examples are, steel bridge components such as hangars, pins and box bar welds; electric power utilities components such as pipe-to-pipe, pipe-to-nozzle, pipe-to-elbow, pressure vessels girth welds, turbine disks, retaining rings, etc.; composite materials for voids, delaminations and inclusions; solid rocket motors for delaminations; storage vessels for corrosion-erosion. Such testing may be for specific local defects, such as, but not limited to, cracks, disbonds, voids or for global material properties such as elasticity, embrittlement, grain structure, etc.

BACKGROUND OF THE INVENTION

The ultrasonic techniques which have application to flaw detection have received wide attention in the past decade with many advances being made in field application of robotic inspection and imaging systems. Such techniques have addressed the problem of inspecting for flaws that are located in regions where ultrasonic inspection is complicated by the fact that a wide variety of flaws must be differentiated from other benign ultrasonic indications. A number of techniques have been devised to detect, discriminate and size such defects, for example, time-of-flight diffraction, synthetic aperture focusing, artificial neural networks and the pattern classification of frequency and time domain waveform features.

The time-of-flight diffraction (TOFD) technique measures the time of reflection of the initial signal from the internal flaw or defect, as well as, the signal reflected from the backwall of the specimen being tested. (see Charlesworth, J. P. and J. A. G. Temple, *Engineering Application of Ultrasonic Time-Of-Flight Diffraction*, John Wiley & Sons Inc., pp 14–15, 1989).

The synthetic aperture focusing technique (SAFT) is a process in which the focal properties of a large-aperture, focused transducer are synthesized from a series of measurements made using a small-aperture transducer which has been scanned over a large area. (see Busse, L. J., H. D. Collins and S. R. Doctor, *Review and Discussion oil the Development of Synthetic Aperture Focusing Technique for Ultrasonic Testing (SAFT-UT)*, Pacific Northwest Laboratory, NUREG/CR-3625 PNL-4957, pp 11 and 16, 1984).

Artificial neural networks (ANN) have been used to generate integrated average measures of microstructural properties of the specimen by examining the power spectral density distributions. (see Thomsen, J. J. and K. Lund, "Quality Control of Composite Materials by Neural Network Analysis of Ultrasonic Power Spectra", *Materials Evaluation*, May 1991, pp 594–600). Note that the RF waveform is required to extract waveform features from power spectral density distributions.

Pattern Classification relies generally on various signal-processing techniques that are well know in the art. (see Shankar, R., P. Jeong, F. Ammirato, L. Nottingham, G. Henry, S. Liu and M. Avioli, "Signal-Processing Applications in the Electric Utility Industry", *Materials Evaluation*, November 1990, pp 1365–1373 and 1391). Also note that two companies, Tektrend (Montreal, Canada) and Infometrics (Silver Spring, Md.) both have commercial products sold under the trademark names of, ICEPAK and TESTPRO, respectively, that implement feature analysis and pattern classification for ultrasonic applications.

A generic requirement of each of these techniques is that the ultrasonic RF signal is digitized at precise position grid points in order to preserve sufficient signal and spatial information to permit subsequent analysis (and reanalysis) using any appropriate signal processing algorithm.

At present, portable ultrasonic inspection is carried out with the use of portable flaw detectors which are operated in a manner similar to standard oscilloscopes and probes, namely, the flaw detector is set down near the test piece and a transducer and cable are connected to it. This poses both a control problem and a display problem.

The control problem arises because the operator typically must use one hand to "scrub" the test piece with the transducer and the other hand for support. This means that the one free hand (non-supporting) is available to either scan the test piece or operate the instrument. The display problem arises whenever the operator cannot place the instrument and the test piece in the same field of view; then, the operator can look at either the transducer or the display, but not both simultaneously. This presents an operational problem in that the operator must keep the transducer stationary, but out of sight, while making instrument adjustments and observing the displayed consequences. Only in ideal situations, such as on a lab bench, can both the transducer and the test instrument be operated simultaneously with two hands in full view of each other.

At present, only simple flaw detectors are sufficiently portable for the applications envisioned. Yet, apart from the operational logistic problems in their use, they offer very limited data recording capability; either RF data is not recorded at all, or if they are, these data are not position referenced nor are they recorded in sufficient quantity to produce useful images.

Computer based ultrasonic imaging systems are typically transportable rather than portable. The smallest such systems weigh about 50 pounds and are not battery powered. One portable system, the Acoustic Crack Detector (ACD), developed for the Department of Transportation about five years ago, represents the current state of the art. However, it suffers from the fact that two operators are required. One is the "up-hole" operator stationed in a mini-van with all of the ultrasonic, computer and electrical equipment. The "up-hole" operator is connected via a long umbilical cable to the "down-hole" operator. The "down-hole" operator scrubs the test piece with the transducer and can only observe a transmitted image on the instrument display, but can not directly control the ultrasonic instrument itself. To effect instrument changes, he must request changes using a voice telecommunication channel with the up-hole operator.

The various instruments that are currently on the market, as illustrated above, have several shortcomings that limit the use of these instruments in some of the most critical environments and areas of limited access. To over come these problems and limitations it would be advantageous to have an instrument that: permits the inspector to view the inspected part and the test image simultaneously; has a semi-automatic scanner so that the inspector only has to move the probe in one direction while motion in the second orthogonal direction is provided by an internal motor; permits a single person to wear the complete system allowing him access to the smallest of areas and the ability to use such a system hands free so that he has two hands to assist him in climbing in tight areas; that has the ability to acquire and store a digital photographic image of the surface being tested; and is totally self contained and does not require attachment to other remote components to complete the system. The present invention provides each of these advantages.

SUMMARY OF THE INVENTION

In accordance with the preferred embodiments of the present invention there is a first embodiment of an ultrasonic test view system for performing non-destructive testing of specimens of engineered materials and structures. This system includes a scanner for delivering and detecting returning ultrasonic signals to and from selected areas of the specimen, processor for controlling the system and processing the returning signals detected by the scanner, and a display for displaying the processed signals from the processor with the display being hands free mountable in front of an eye of a user of the system.

In a second embodiment of the present invention is a semiautomatic scanner for use with and controlled by an ultrasonic test view system for positioning a probe at various locations within a selected region of a specimen of engineered materials and structures. The scanner includes a housing that contains the components of the scanner, a transport system to provide motion to the scanner along a first path of the selected region of the specimen in response to signals from the ultrasonic test view system. In addition there is a manually translatable arm movably affixed to the housing that has a coupling device at its distal end that is disposed to receive the probe for manually transporting the probe along a second path of the selected region of the specimen by the user of the scanner. Coupled to the arm there is an encoder to determine the position of the probe along the second path and for reporting positional information to the ultrasonic test view system.

In a third embodiment of the present invention there is an ultrasonic test view system for performing non-destructive testing of specimens of engineered materials and structures that includes a processor to control the system and to process test information, an ultrasonic probe under control of the processor to deliver ultrasonic signals and detect returning ultrasonic signals to and from selected areas of the specimen. Additionally, there is a semiautomatic scanner coupled to the processor to position the probe at various locations within a selected region of the specimen. The scanner includes a housing that contains the components of the scanner, a transport system to providing motion of the scanner along a first path of the selected region of the specimen in response to signals from the ultrasonic test view system. In addition there is a manually translatable arm movably affixed to the housing that has a coupling device at its distal end that is disposed to receive the probe for manually transporting the probe along a second path of the selected region of the specimen by the user of the scanner. Coupled to the arm there is an ,encoder to determine the position of the probe along the second path and for reporting positional information to the ultrasonic test view system.

In accordance with a third embodiment of the present invention there is an ultrasonic test view system for performing non-destructive testing of specimens of engineered materials and structures. This system includes a scanner to deliver ultrasonic signals and detect returning ultrasonic signals to and from selected areas of the specimen, a processor to control the system and process the returning signals]s detected by the scanner. The processor includes a voice recognition device to detect and translate voice commands to select and control the operations of the processor. Additionally, the system includes a microphone for the user to deliver voice commands to the voice recognition device.

The fourth embodiment is of yet another ultrasonic test view system for performing nondestructive testing of specimens of engineered materials and structures. This system includes a scanner to deliver ultrasonic Signals and detect returning ultrasonic signals to and from selected areas of the specimen, a processor to control the system and process the returning signals detected by the scanner. Here the processor includes a memory device for storing the returned and corresponding processed signals and the system set-up parameters.

The fifth embodiment of the present invention is of an ultrasonic test view system for performing non-destructive testing of specimens of engineered materials and structures that includes a scanner to deliver ultrasonic signals and detect returning ultrasonic signals to and from selected areas of the specimen, a processor to control the system and process the returning signals detected by the scanner, and a battery for powering the system to make it fully portable.

A sixth embodiment of the present invention is of an ultrasonic test view system for performing non-destructive testing of specimens of engineered materials and structures that includes a scanner to deliver ultrasonic signals and detect returning ultrasonic signals to and from selected area of said specimen, a control subsystem to control the operation of the system, a processor coupled to the scanner to process the returning signals detected by the scanner, and a case to enclose the processor and control subsystems with the case being sealed to protect the internal components from contamination.

BRIEF DESCRIPTION OF THE FIGURES

FIGS. 2a–d are a set of plan views of a semi-automatic low profile scanner of the type that may be used with the system of the present invention.

FIG. 16 is a table to illustrate the correspondence between an example set of spoken commands and mouse or keyboard entered commands.

DESCRIPTION OF THE PREFERRED EMBODIMENTS

Definitions

In the following discussion of the present invention several terms that are well known in the industry will be used. For purposes of understanding the following discussion, without having to resort to reference material, a brief definition is given here for some of those terms:

A-scan: Is a rectified amplitude versus reflection time plot of the applied signal and the reflected signals from defects and the backwall of the specimen.

RF Display: Is similar to A-scan displays with the pulses displayed as oscillating frequency (radio frequency) responses instead of the rectified signals of the A-scan display.

B-scan: Is a cross-sectional, or side, view of a specimen tat illustrates in two dimensions the distance from the sound entry surface to the reflector surface using the refraction angle, pulse amplitude and travel time information of the specimen.

C-scan: Is a two dimensional top, or plan, view of a specimen that shows the outline of an interior defect without showing the depth of the defect.

System Description

Figure 1:
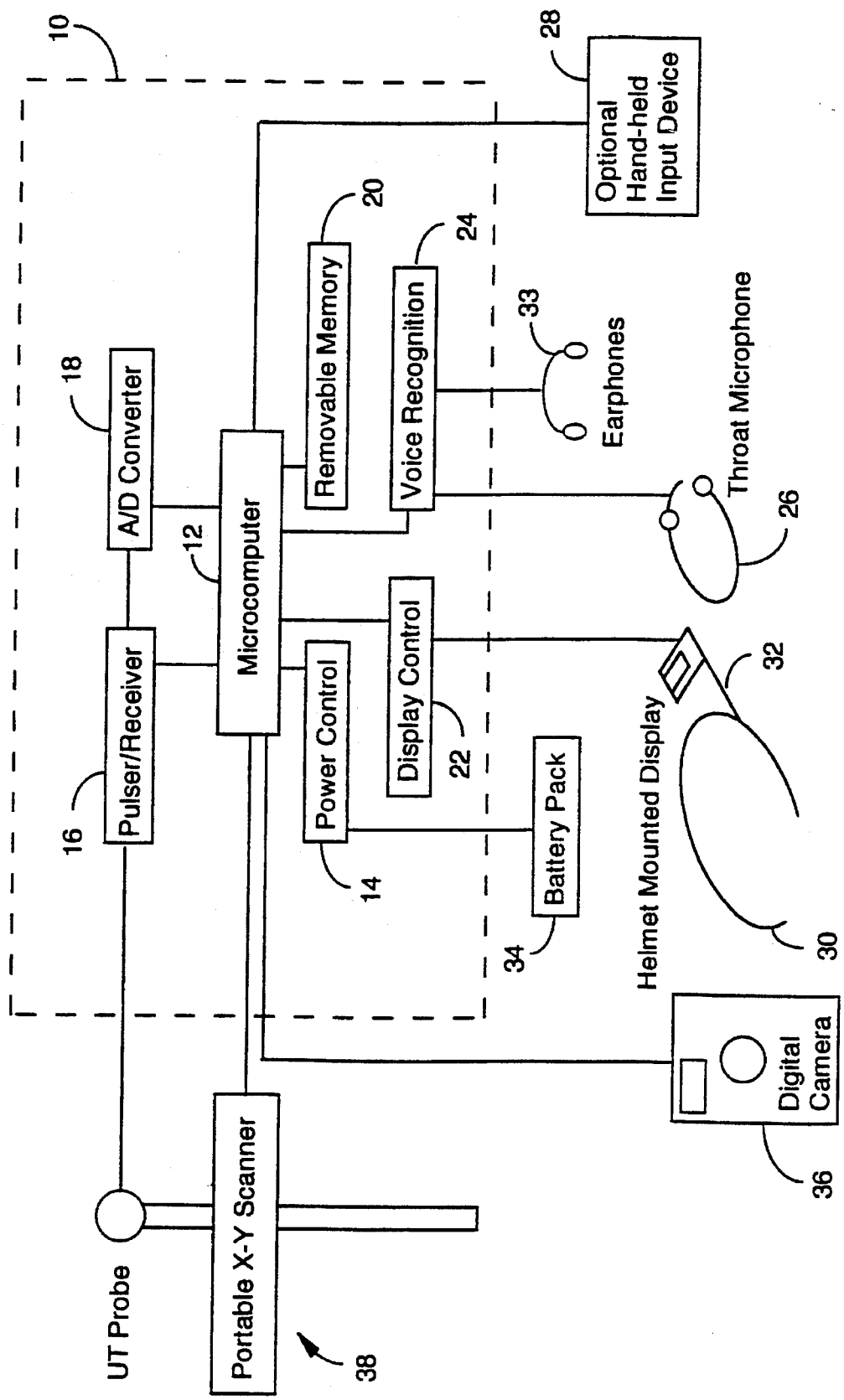
FIG. 1 is a block diagram of the HF-UTV of the present invention.

FIG. 1 shows a block diagram of the HF-UTV of the present invention that is designed to serve as both an ultrasonic signal recorder and imaging system in a small, portable package. Because the system of the present invention is fully integrated, portable and designed for use by a single inspector, various portions of the system are worm on the inspectors back, neck, head and waist or stored in pockets as will be specified as the various elements of the block diagram are introduced.

A backpack 10 to be carried or worn on the inspector's back includes the computer and memory elements of the system of the present invention. Backpack 10 contains microcomputer 12, power control circuit 14, ultrasonic pulser/receiver 16, analog-to-digital converter 18, removable memory unit 20, display controller 22, and voice recognition processor 24. In the experimental unit an aluminum case with a hinged lid was selected for use as backpack 10. Straps were added to a standard 9×14×3 inch aluminum case to support it on the inspector's shoulders and hips. An example of such a case is a Zero rectangular box ZT150-224-72 and cover ZT150-224 COT5.

With the power conserving features discussed above in combination with the use of a metal back pack 10, the back pack 10 can serve as a heat sink and the thermal build-up is limited by the power conservation techniques. Additionally, if back pack 10 is sealed and made water proof, the inspection system of the present invention can be used underwater because it is self-contained.

The computer system contained in backpack 10 includes board level subsystems interfaced to a standard computer buss, such as the IBM Industry Standard Buss (ISA). Power control circuit 14 controls and gauges battery charge and conserves power by switching critical components off or to low power mode while not in use or in the dead-time between data acquisitions. In particular, in the prototype unit of the present invention the 5 volt power supply to A/D converter 18 and/or pulser/receiver 16 are only powered during data acquisition and they are switched off between acquisitions. Additionally, the general purpose microcomputer 12 supports general purpose Centronics parallel and RS-282C serial interfacesto peripheral devices and other computer systems.

Microcomputer 12 is a PC/AT compatible with a CMOS CPU, on-board RAM, serial and parallel I/O ports, solid-state memory that emulates a small disk drive and a built-in timer. The solid-state memory is used to store the computer program and its support files. An example of a computer that could be used with the present invention is an Ampo, Core Module/286; Ampro Mini Module/FSI-Floppy/IDE controller, Serial, Parallel.

Power control circuit 14 is provided to conserve the use of power in the system by turning the power to various of the subsystems off when they are not in use, namely, between data acquisition pulses or after a specified period of inactivity. By so doing the life of the batteries on a single charge can be greatly extended. For example, by doing so with the pulser/receiver 16 and ADC 18 it is estimated that there will be a 50% power reduction. Power control circuit 14, for example, may be a 12 v to 5 v DC converter that is switched on by microcomputer 12 for data acquisition and off when a time out period of inactivity is exceeded or at the end of each data acquisition.

Pulser/receiver 16 pulses ultrasonic transducers 38 and receives signals generated by ultrasonic transducer 38. Further, pulser/receiver 16 is fully digital and completely under software control to ensure ease of setup and a high degree of repeatability. The pulser section can produce a positive or negative square-wave pulse that is synchronous with an external trigger or computer generated command. The pulser output voltage, pulse damping, pulse polarity, number of pulse cycles, pulse width are each fully adjustable. The receiver section gain and attenuation are adjustable; high and low pass filters are selectable. An example of such a pulser/receiver is an Adaptronics model GRC PCPR-100.

Analog-to-Digital Converter (ADC) 18 digitizes high frequency ultrasonic transient signals from pulser/receiver 16 and buffers them in local high-speed memory. ADC 18 can have different maximum sampling rates and sampling resolutions for different applications. However, a 25 MHz 8-bit ADC is adequate for most field inspection applications using transducers up to 5 MHz. ADC 18 is fully digital and completely under software control to ensure ease of setup and a high degree of repeatability. The sampling rate, trigger selection, clock selection, threshold phase and level are all adjustable. Additionally, ADC 18 can transfer information from its local memory to memory within microcomputer 12 for storage and analysis. An example of an ADC that could be used in this application is a Sonotek model STR-825 25 MHz A/D.

Removable memory 20 can be, for example, either a standard 3.5-inch floppy disk and drive or a removable solid-state PCMCIA compatible solid State "credit card" and drive. Removable memory 20 is provide to store digitized ultrasonic data, images and setup information for permanent storage and later analysis. An example of such a memory unit is a TEAC 3.5-inch floppy disk drive model FD234HF217.

Voice recognition processor 24 is a complete voice input/output device that recognizes speech sounds and responds by sending corresponding codes to the computer. The voice subsystem can also synthesize speech for audible feedback to the operator via earphones 33 for prompting, verification and error conditions. An example of a voice recognition processor that might be used with the present invention is a Voice Connection, Introvoice Pro-module.

Around his neck the inspector wears a throat microphone 26 either outside or inside his collar for protection from the environment and from becoming a hazard by snagging on a surface while the inspector is moving or climbing into position. Microphone 26 interfaces with voice recognition processor 24 in backpack 10 and is used to communicate hands-free with the computer system when the computer is in the voice recognition mode. In that mode voice recognition processor 24 accepts input instructions from the microphone 26 and translates them into computer commands or menu selections. While voice recognition is currently dependent on the accent and diction of the individual that is speaking, voice recognition processor 24 can be programmed to accept input instructions from various users in any language. FIG. 16 illustrates the correspondence between an example set of spoken commands and their mouse, keyboard and scroll function counter-parts. Microphone 26 may be a throat mike for high noise environments or a standard head or helmet-mounted microphone. An example of a microphone that could be used for this application is a Racal Acoustics model SEC7535GP.

Earphones 33 also interface with voice recognition processor 24 to provide the inspector with monaural or binaural feedback regarding the state of the system and can provide feedback messages to assist or simplify operation. Further, microphone 26 and earphones 33 may also be used in conjunction with telecommunication equipment to allow remote communications between the inspector and local or remote support personnel. An example of earphones that could be used in this application is a Racal Acoustics model SEC7535GP.

A safety helmet 30 worn by the inspector, since most of the inspection sites will be such that the state health and safety code or federal regulations will require a helmet, provides a convenient platform on which to mount a visual display 32. In the present application visual display 32 is mounted to one side of the helmet forward of one of the eyes of the inspector to ideally present a 12 inch virtual image that appears to float a few feet in front of the inspector. The position of display 32 should be adjustable so that the each inspector can select the most suitable position.

Mounted in this way, display 32 can be worn in a "bifocal" position. In this position, it does not block the direct line of sight of the wearer, but is visible by simply glancing down. Alternatively, display 32 can be placed directly in front of the eye, so that with a few minutes practice, the inspector can see both the specimen being scanned and the display image simultaneously, using both eyes, thus presenting a superimposed image to the inspector's brain.

In the experimental tests of the system of the present invention a unit that displays 640×200 pixels, or 25 lines of text with 80 characters per line, using high contrast red LEDs on a black background was selected. The quality and contrast of the unit used in those tests substantially exceed that of a standard CRT display and is suitable for indoor or outdoor viewing. These displays also include a focus knob to accommodate individual vision characteristics.

There are a variety of small visual display units available that will lend themselves to this application. These display units are typically 1.5×1.3×3.5 inches and weigh less than four ounces. The overlapping left and right visual fields results in a composite visual display that appears to the observer as though the test display is a transparent overlay on the visual image of the part surface. An example of such a miniature display is a Reflection Technology Private Eye which is supplied with an interface board, MiniModule/Private Eye, for inclusion in backpack 10 as display control 22.

If the inspector were to have vision in only one eye, or choose to only use one eye, it would still be possible for that inspector to use the system of the present invention. In this situation the inspector clearly could use the display in the "bifocal" position, or if a display having the capability of projection the display image on the same eye that is viewing the specimen, the superimposed image can also be achieved.

Various other components, some of which the inspector uses in his hands, are stored for convenience on a utility belt worn around the inspector's waist or in a pocket. One of the components worn around the waist is a rechargeable battery pack 34 to power all of the components of the system by interfacing with power control circuit 14 in backpack 10.

The waist was selected because battery pack 34 tends to be bulky, and little on the heavy side, and the waist is close to the wearer's center of gravity. This is an ideal position for maneuvering extra weight with comfort and balance. Further, since it is not necessary for the inspector to handle, open, or recharge, battery 34 during the actual inspection operation, the waist location also presents an out of the way location for battery 34.

Battery packs 34 may have different capacities (and weights) as the inspection job requires. For most applications the experimental tests indicate the life of a battery charge should be about 4 hours for typical operation. The system is powered by a standard commercial 12-volt power belt with an integrated battery charger.

Battery pack 34 consists of a portable 12-volt battery pack with individual batteries stored in separate compartments. In the present invention the design that is preferred includes batteries that may be added or substituted for batteries of greater capacity. Additionally, there is a charger contained in a compartment of the battery pack that uses a standard cigarette lighter compatible connector to allow recharging in the inspector's vehicle. An example of a battery pack that can be used with the present invention is a VDO-PAK Power Belt model SP-650 with a charger.

As an alternative to voice commands, a hand-held input device 28, such as a keyboard or simple pointing device (e.g. a trackball or cursor position keypad), may be used in addition to or instead of microphone 26. Such a device would interface directly with microcomputer 12 in backpack 10 via of the parallel or serial interfaces. While not in use this device could be stored in a pocket or on a utility belt around the waist of the inspector.

The system of the present invention could also be used in the laboratory with a keyboard, mouse or trackball, for example, in place of the optional hand-held input device 28 shown in FIG. 1.

Another item that might be stored on the inspector's utility belt between usages is a battery powered digital still video camera 36 which interfaces with microprocessor 12 in backpack 10 by either a standard parallel or series interface.

By providing the inspector with digital camera 36, he may acquire photographic imager of the inspection site and surface. These visual images may be uploaded to the HF- UTV and stored in removable memory 20 on disk, or another medium, together with the setup and waveform information produced during the inspection. The HF-UTV uses a novel approach to increasing the confidence in the documentation, namely, it links the digital photographs of the inspected surface area to the ultrasonic data and the setup. A composite view of an ultrasonic C-scan image and a visual image of the inspected surface, such as might be obtained with the digital camera, is shown in FIG. 3. Other information, such as text annotation, setup information and critical A-scan waveforms may also be placed on the composite image. This combination of setup, digitized ultrasonic data and visual record of the inspected area provide an unambiguous record of the entire inspection process and reduces uncertainty in decision-making based upon ultrasonic inspection, facilitates repeatable re-examination and provides an accessible database for future reference and analysis.

Figure 3A:
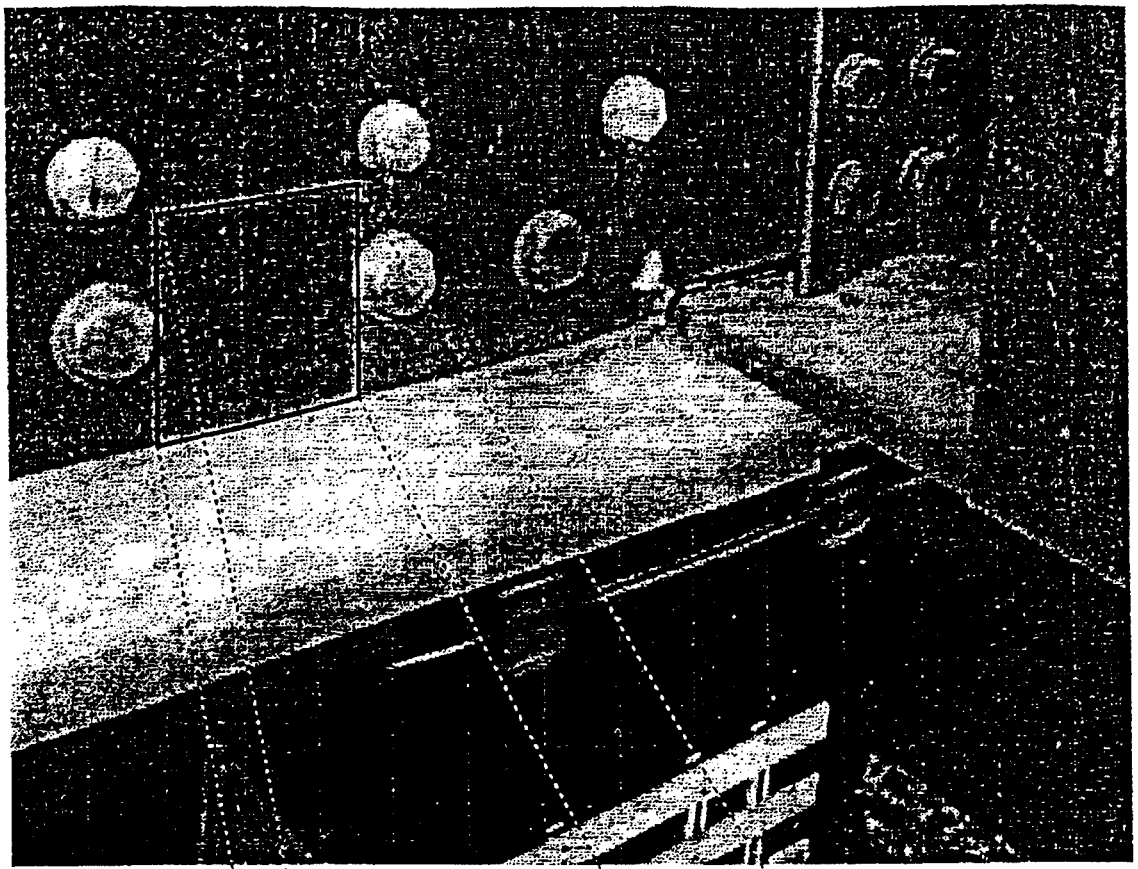
FIGS. 3a and 3b are composite views of a visual surface image of the inspected interior surface of a longitudinal girder of a structure such as a bridge and an ultrasonic C-scan image of the outlined portion of that structure, respectively.
Figure 3B:
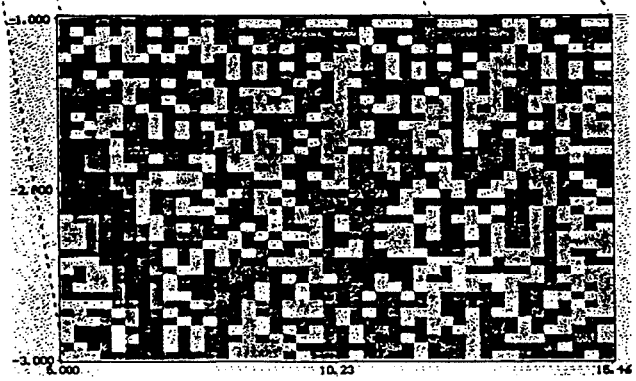

FIGS. 3a and 3b are composite views of a visual surface image of the inspected interior surface of a longitudinal girder of a structure such as a bridge and an ultrasonic C-scan image of the outlined portion of that structure, respectively. FIG. 3a is typical of the image that the inspector may decide to capture and record with digital camera 36 so that it can be viewed when the C-scan information of that component is examined later in the laboratory. The recording of the photograph of the work site also makes it possible to better identify the work site if it is necessary to revisit the work site for additional tests.

Digital camera 36 is a small portable solid-state digital still camera that can store gray-scale snapshots in its internal memory. Captured images may be transferred directly to microcomputer 12 via a serial interface and automatically linked to the appropriate ultrasonic data and setup files. An example of such a camera is a Logitech Fotoman.

The last item of the inspection system of the present invention is an ultrasonic test (UT) probe and scanner 38 which interfaces with microcomputer 12 in backpack 10 by a standard parallel or series interface, and is mountable on the inspector's utility belt when not in use. The probe may vary to meet the demands of a particular application or test area, however, the probes used with the present invention can be of any single or dual element ultrasonic transducer that is readily available. The portable scanner is typically a 2 or 3 axis semi-automatic scanner with the automatic axis, or multi-axis path (e.g. helix, curve, or irregular path over a surface that is other than flat) being the low power axis or path that is driven by a stepper motor or DC servo motor, as desired. The position encoding may be either incremental or absolute.

The axes or paths of the scanner are typically controlled as follows:

X-axis is linear, motorized and encoded;

Y-axis is linear and encoded; and

Z-axis is rotational, encoded and may be optionally motorized.

The system of the present invention can accept pulse echo or pitch-catch search units and can be operated as a manual UT flaw detector and recorder; alternately, the system supports a parallel or serial interface to a manual, semi-automatic or automatic scanner. FIG. 2 shows a semi-automatic low profile scanner 38 of the type that may be used with the system of the present invention.

The pulse-echo method can use a single search unit that both transmits ultrasonic pulses into the test specimen and receives the reflection of these pulses from discontinuities or surfaces in the specimen. The pitch-catch method uses two search units, one to transmit and one to receive. If these two transducers are located On opposite sides of the test specimen, this technique is referred to as the through transmission method.

Inspection Documentation

The HF-UTV is completely computer controlled and has no additional manual controls. Rather the state of all of its controls, or "setup", are fully programmable and recorded with each scan. Therefore, a complete record of the inspection process is always associated with each set of scanned wave forms to facilitate repeatable inspections. Setup information is recorded using Electric Power Research Institute (EPRI) Digital Recording of Ultrasonic Signals (DRUS) format to facilitate future data review and the transfer of information between systems (EPRI report NP-2586). For this reason, only printable ASCII characters are used. Some of the setup information is provided automatically by the computer, some information is prepared in advance by the inspector and some is automatically supplied by the computer. Computerized setups such as this eliminate the need for ancillary handwritten records and increase the confidence in inspection data and documentation.

One Man Operation

Because of the relatively high level of integration, system power, ultrasonics, data acquisition, imaging and data storage in a completely self-contained and portable unit, the entire system can be voice operated by a single person. This architecture reduces transportation and setup costs because no up-hole or down-hole interconnections are required. Furthermore, nearly all of the otherwise large number of discrete subsystem interconnections, which must be made at each inspection site with the prior art instrumentation, are eliminated because most of the subsystems are contained within the backpack and are permanently interconnected.

The portability of the HF-UTV permits access to all parts of bridge structures, for example, box beams, high structures, backup bars and close or difficult to pass structural members. The backpack may be worn on the front or back and may be easily removed and hand-carried using the hand strap to facilitate traversing obstacles. All other HF-UTV components are either carried in a vest, for example, transducers and couplant, or may be worn in a holster around the waist, for example, manual scanner and battery pack. The display itself may be easily carried in a vest pocket and worn on the hard-hat only during inspection time. The few cables to the backpack are easily routed through clothing to prevent snagging peripheral devices.

FIGS. 2a–2d show various views of a low profile scanner 38 of the type that lends itself to use with the present invention. FIGS. 2a and 2b show a top and side view, respectively, and FIGS. 2c and 2d show the end view of the scanner with arm 60 in two different positions. Scanner 38 includes a rear housing 40, a front housing 44 and an arm 60. Rear housing 40 includes powered trucks each having at least two wheels which provide movability for the entire scanner assembly in the low duty cycle path. Front housing 44 includes an encoder 48 for determining the actual extended (horizontal) position of gimbal 62 on arm 60, a motor 52 and a gear box 50 coupled to trucks 42 to provide movement to scanner 38 in the low duty cycle path. Attached to the distal end of front housing 44 are rollers 54–58 on which arm 80 is mounted. Rollers 54 and 58 are idlers and roller 56 is attached to a shaft of encoder 48 to provide positional information with respect to gimbal 62 at the distal end of arm 60. Gimbal 62 is designed to support the UV probe (not shown) over the region of the specimen being examined.

FIGS. 2c and 2d show arm 60 and rollers 54–58 in two different positions with respect to horizontal. Arm 60 and rollers 54–58 are rotational mounted to the distal end of front housing 44 to allow the probe mounted on gimbel 62 to ride over a surface that is not flat. Arm 60 is free to rotate through at least 30° to accommodate various surfaces.

Since the system of the present invention is a self-contained, one-man operational, battery powered system, one of the techniques for reducing the power usage, and therefore extending the time during which testing can be performed, only the motion of scanner 38 in the x-direction, or low duty cycle path, is powered. In an x-y grid scanning mode the probe is moved incrementally in one direction and the scanner housing then remains in that position relative to the path of that position while the probe is manually moved continuously through the range of the grid being examined in the second path, then scanner 38 is again advanced incrementally while the probe is continuously passed manually in the reverse direction along the next path in the second direction. Thus, it can easily be seen that the first path, which we have called the x-direction for convenience, require less power to effect the necessary movements due to the low duty cycle of that movement than will be required for the continuous motion in the second direction, which we have called the y-direction for convenience. Thus, the x-direction movement is produced by motor 52 under the control of microcomputer 12 in conjunction with encoder 48 which indicates when the y-direction motion in each pass is complete. Arm 60 is manually moved by the inspector to save energy. Since there is a constant position encoded signal available to microcomputer 12, the speed and uniformity of movement of arm 60 need not be constant.

Additionally, to prevent scanner 38 from slipping out of position and to keep its directional advancement linear, several techniques might be used. One technique when inspecting steel structures is to have magnetized wheels as part of trucks 42. Additionally, a ferritic track can be placed on the surface along which scanner 38 is to be advanced and the magnetic wheels following that track. Several techniques can be used to hold the tracks in place including a temporary adhesive or straps. Alternatively, a vacuum system might be employed, or some form of adhesive track laid down (e.g. double sided taped on which the wheels advance or mating Velcro surfaces on the face of the wheels and the surface over which scanner 38 is advanced).

The use of a semi-automatic X-Y scanner is unique in providing high resolution data acquisition with low power requirements. One path is manually operated; the other path is motorized. Both axes are position encoded. The use of a semi-automatic scanner provide the high resolution associated with a fully automated scanner, but without the associated power costs; also it provides the portability and low power consumption of a manual scanner without suffering low user productivity. Automatic scanners are generality used whenever ultrasonic imaging is required; imaging typically implies that some ultrasonic waveform feature is plotted as a function of transducer position, and therefore, position must be precisely controlled and recorded with each ultrasonic waveform.

For example, the ultrasonic B-scan is a 2-D plot of the signal amplitude, which is usually color or gray scale coded, as a function of transducer linear position along the horizontal display axis and as a function of time-of-flight of the signal echo along the vertical display axis. The resulting image is a cross-sectional ultrasonic image along the transducer path of motion. Another common ultrasonic image is a color coded plot of a signal statistic as a function of the X-Y transducer position on the surface of the inspected part. The most common such statistics are the peak amplitude of signal or the time of a threshold crossing in a gated portion of the signal, although any statistic is possible and more than one gate may be used to construct the signal feature. The resulting image is a top or plan view of the part within a "strata" of interest.

When it is desirable to generate an image, automated scanners are preferred because image data are a function of transducer position and it is tedious to manually acquire the same data with the same accuracy and quantity. A computer can repeatably position a transducer relative to the test part and is limited primarily by the repeatability of the position encoders and mechanical hysteresis. This means that tests can be repeated at different gains, without introducing another source of position error. On the other hand, a manual scanner with identical position encoders will not produce the same repeatability in the same amount of time as an automatic system. In order to see this, consider how an automatic ultrasonic test system is programmed to acquire data. With an automatic scanner, the system generates a table of X and Y grid points at which to acquire data. The system motion controller then moves the scanner until, based upon closed loop motion control, it reaches each successive point in the X-Y table. Usually a small spatial tolerance region about the target point is specified by the operator to eliminate wasteful "hunting" motions at or near the resolution of the encoders themselves. With a manual scanner, the position control is provided by the "man-in-the-loop". The operator cannot provide the same control precision as rapidly because he cannot sample position information or respond as rapidly. In addition, the automated system can operate each axis independently whereas the operator cannot. An automated system simply halts (and looks) each axis as the target value is obtained and then continues to seek the target value for the other axis. Therefore, in order to scan efficiently, manual systems trade-off a larger tolerance region for scanning speed.

Our solution to the position tolerance-productivity tradeoff associated with manual scanning, is to use a semi-automatic scanner with one axis constrained. Therefore the operator, in scanning from one end of the free axis to the other, must cross each target point. Note that the tolerance region is the same as that for the automatic system. The only additional source of error depends upon the computer speed in processing and responding to the position of the free axis and the velocity of the free axis. Because the computer speed is very fast relative to the manual scanning speed, inevitable variations in manual scanning speed generally have very small and controllable impact on positioning repeatability.

In addition to several basic data acquisition methods, the system supports a new data acquisition method we refer to as "ruled" data. In order to understand the benefits of ruled data, a description of the other types of data acquisition are given first.

Timed scan are ultrasonic waveforms that are acquired at equal time intervals on systems that do not provide any position encoding. Typically, the operator initiates the data acquisition sequence with a start command and a waveform is acquired every k seconds until the system storage capacity is reached or the operator issues the stop command. Timed data acquisition may be used to obtain an approximate B-scan or C-scan on a system that does not have position encoding by moving a transducer on a straight line at a constant velocity on the part surface. The position accuracy is limited by the operator's ability to scan at a constant velocity and direction. Timed data can be acquired very rapidly and with a minimum of equipment setup if an approximate line scan is desired.

Measured scan are ultrasonic waveforms that are acquired on demand on systems that do not provide any position encoding. Typically, the operator initiates the acquisition of each waveform with a separate command. Measured data acquisition may be used to obtain an approximate B-scan or C-scan on a system that does not have position encoding by placing a transducer on predetermined (measured) grid points marked on the part surface. Because the time of data acquisition is completely under operator control, the position accuracy is only limited by the operator's ability to measure, mark and position the transducer on each mark. Measured data are acquired more slowly and accurately than timed data.

Manual scan are ultrasonic waveforms that are acquired with a system that relies on the operator to move the transducer and uses position encoders to determine when to acquire data. Manual scan data acquisition can be used to obtain B-scan or C-scan in a manner similar to automated scans, however, because of the man-in-the-loop problem, positioning repeatability is a problem (as discussed above).

Automated scan are ultrasonic waveforms that are acquired with a system that automates the motion control of a transducer and uses position encoders to accurately define the position at which data are acquired. Automated data acquisition are used to obtain a B-scan or C-scan by using a computerized motion controller to position a transducer at user defined grid points that have been input to the system as part of the system setup process. Each waveform s digitized when all scanner axes intersect user defined grid lines in the scan aperture. Fully automated scanning can be supported but reduces the portability of the system because of scanner weight, cabling and power requirements. Fully automated data are acquired the most rapidly and accurately, however, system setup time may make this method of data acquisition inefficient for testing small separate areas of interest.

Ruled data are ultrasonic waveforms that are acquired at prescribed encoder positions along a free manual axis of a multi-axis scanner. Only one axis at a time is in motion during a scan; all the other axes are constrained except between each scan line when they are "indexed" to the position of the next scan line. The scanner may be semi-automatic or manual, as long as the non-scanning axes can be locked, either under motor control or by using mechanical detents. The position accuracy is limited by encoder resolution, mechanical coupling and scanner positioning, all of which can be repeatably characterized. The simplest form of ruled data can be acquired with a semi-automatic multi-axis scanner in which all axes are position encoded and all but one of the axes are automatically controlled (and therefore mechanically constrained) with a motor while the uncontrolled axis is manually scanned along a determined line. Ruled data are acquired nearly as rapidly as timed data and with the same position accuracy as the fully automated method. To obtain these benefits, a small scanner (carried in a holster) must be carried and setup on the test piece.

Figure 6A:
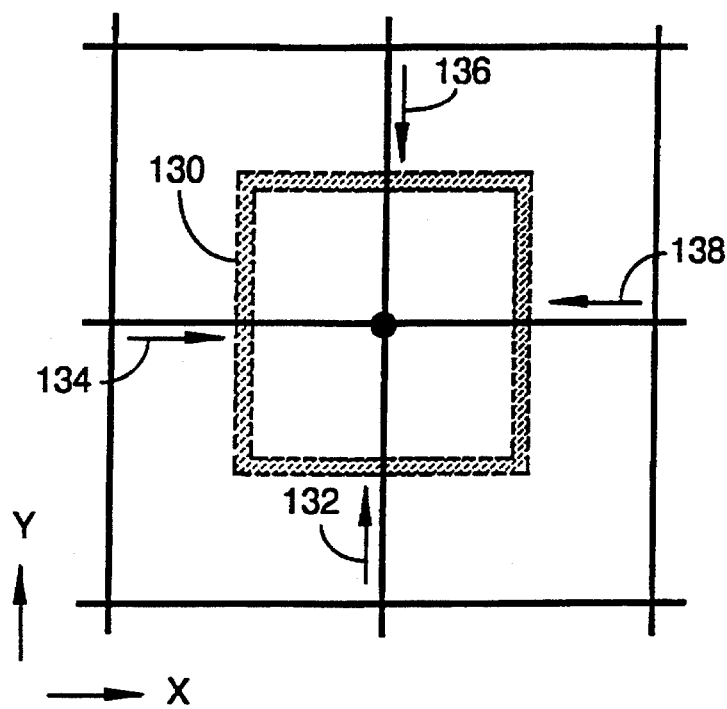
FIGS. 6a and 6b illustrate the area of uncertainty when a grid is freehand and ruled scanned, respectively.
Figure 6B:
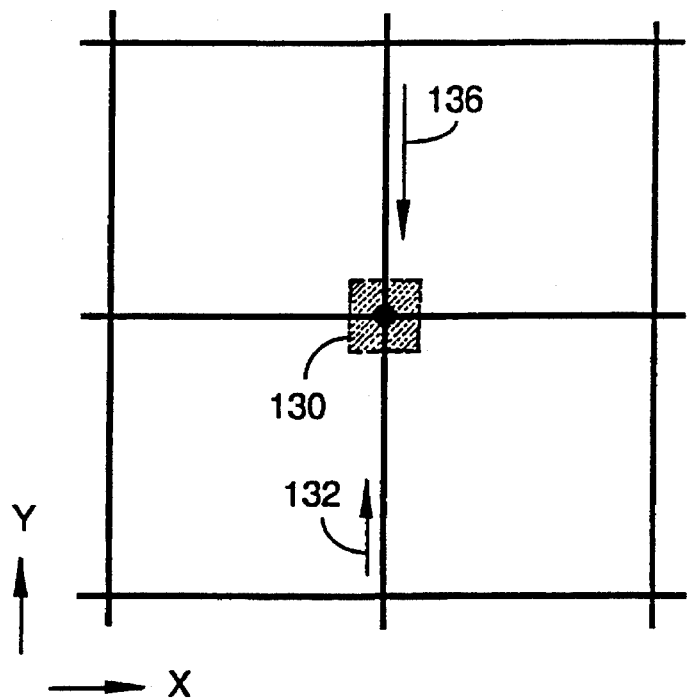
Figure 7:
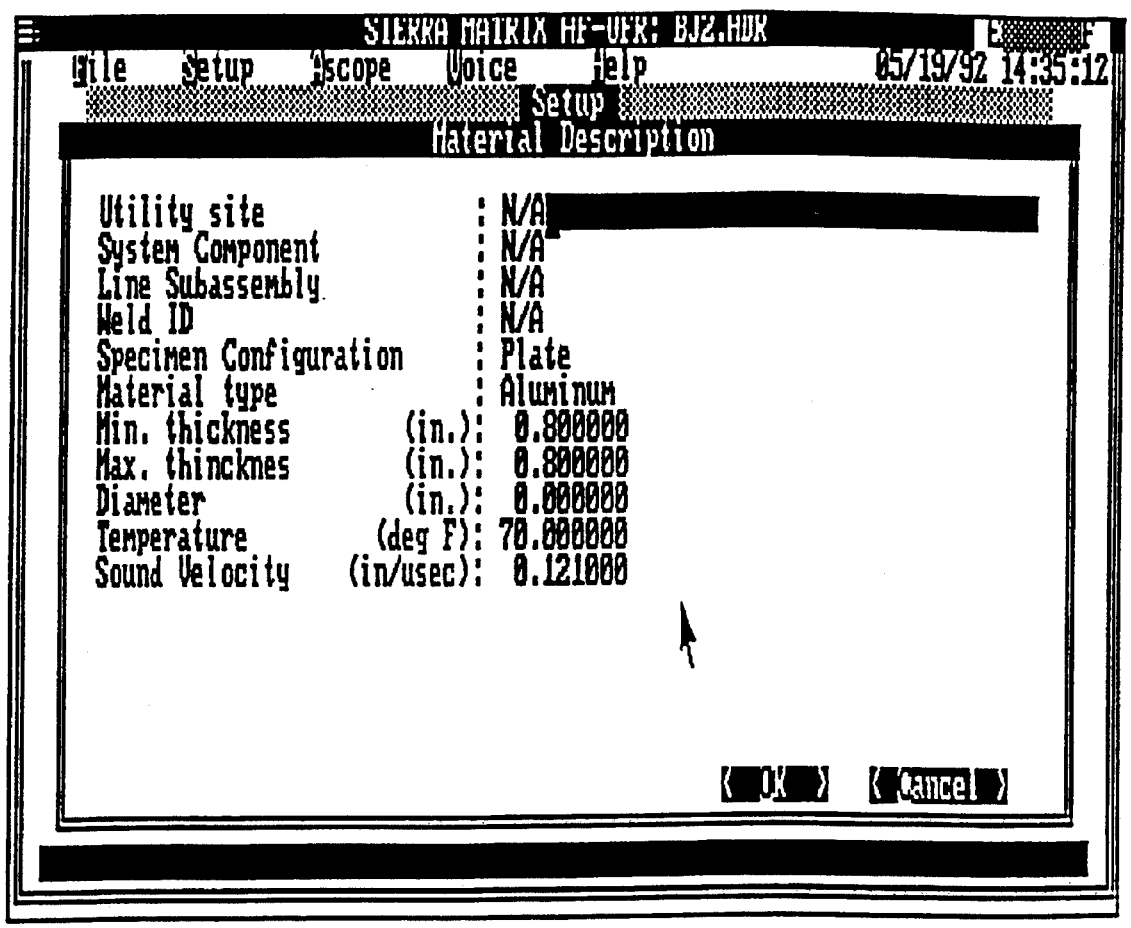
FIG. 7 is a set-up menu of the present invention for the specimen material description.
Figure 8:
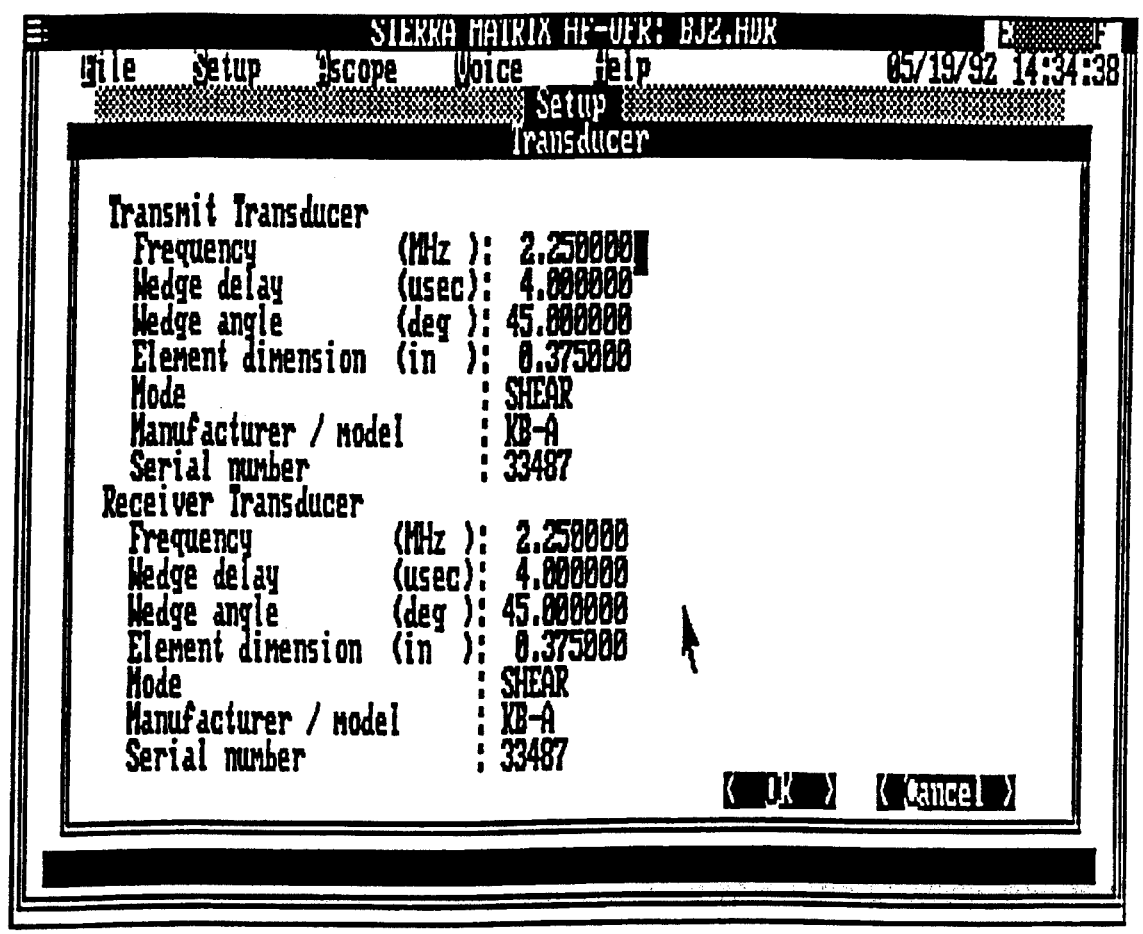
FIG. 8 is a set-up menu of the present invention for the transducer description.
Figure 9:
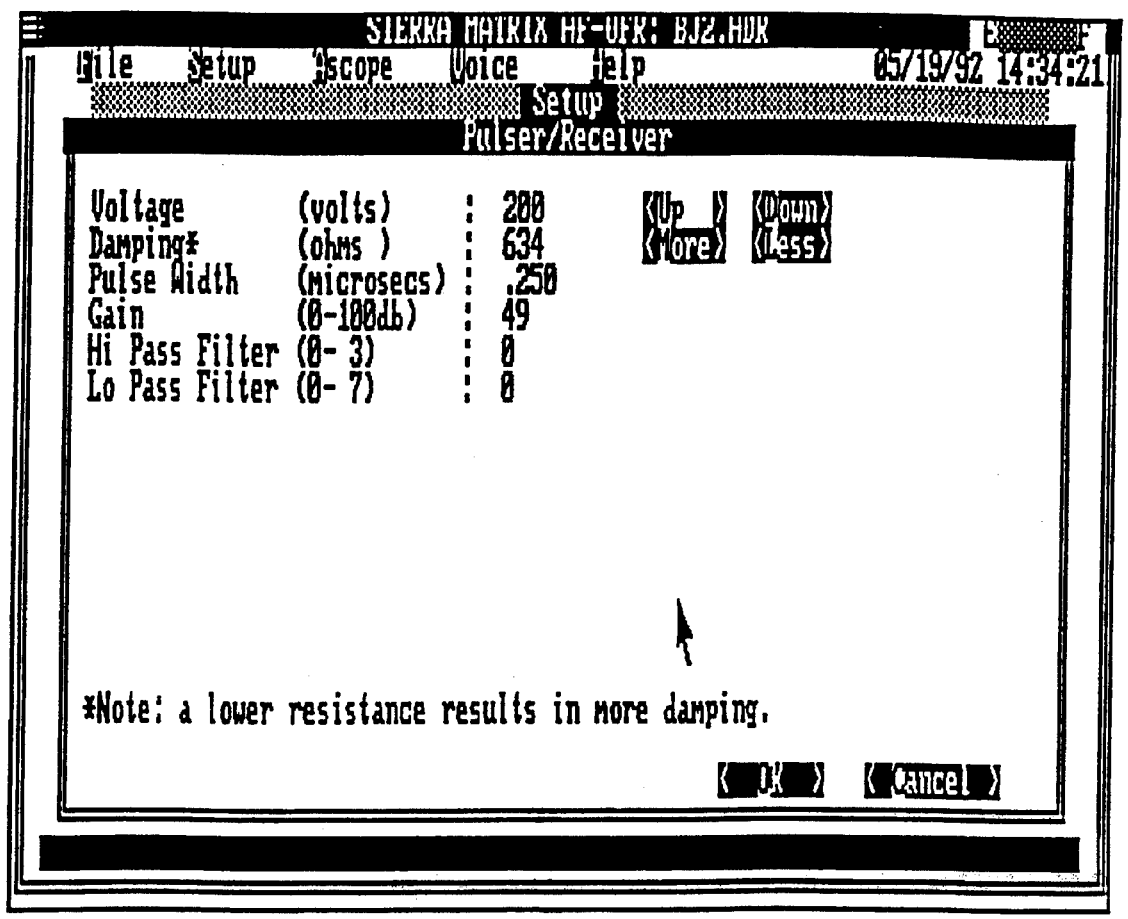
FIG. 9 is a set-up menu of the present invention for the pulser/receiver description.
Figure 10:
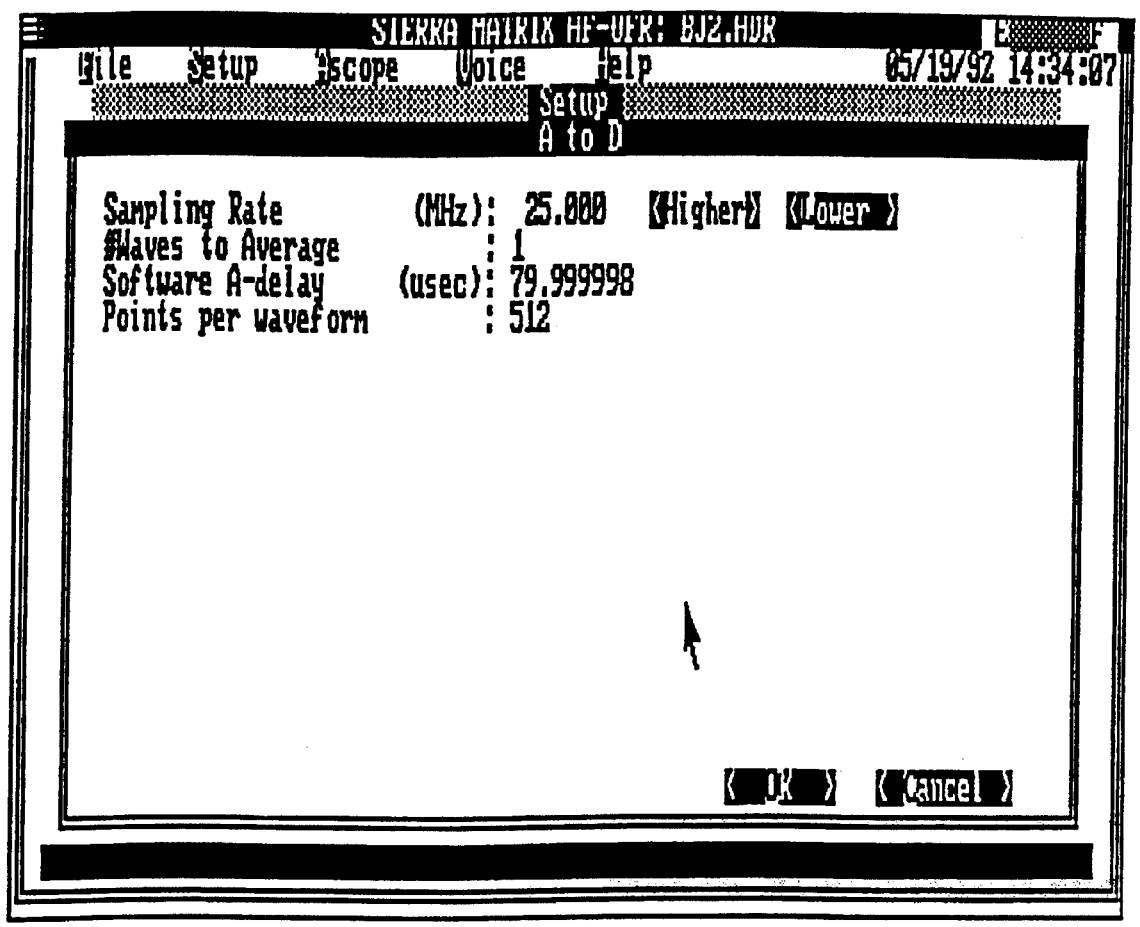
FIG. 10 is a set-up menu of the present invention for the A/D description.
Figure 11:
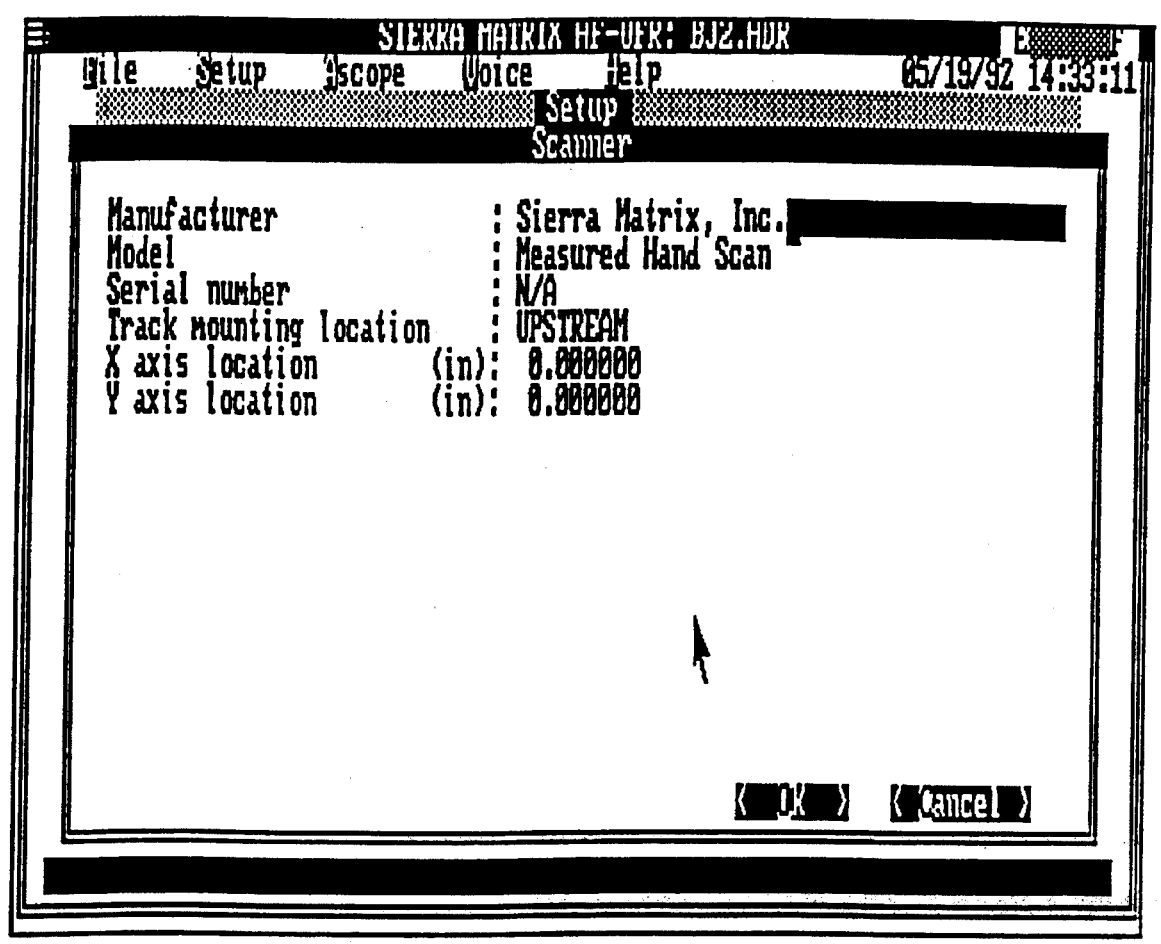
FIG. 11 is a set-up menu of the present invention for the scanner description.
Figure 12:
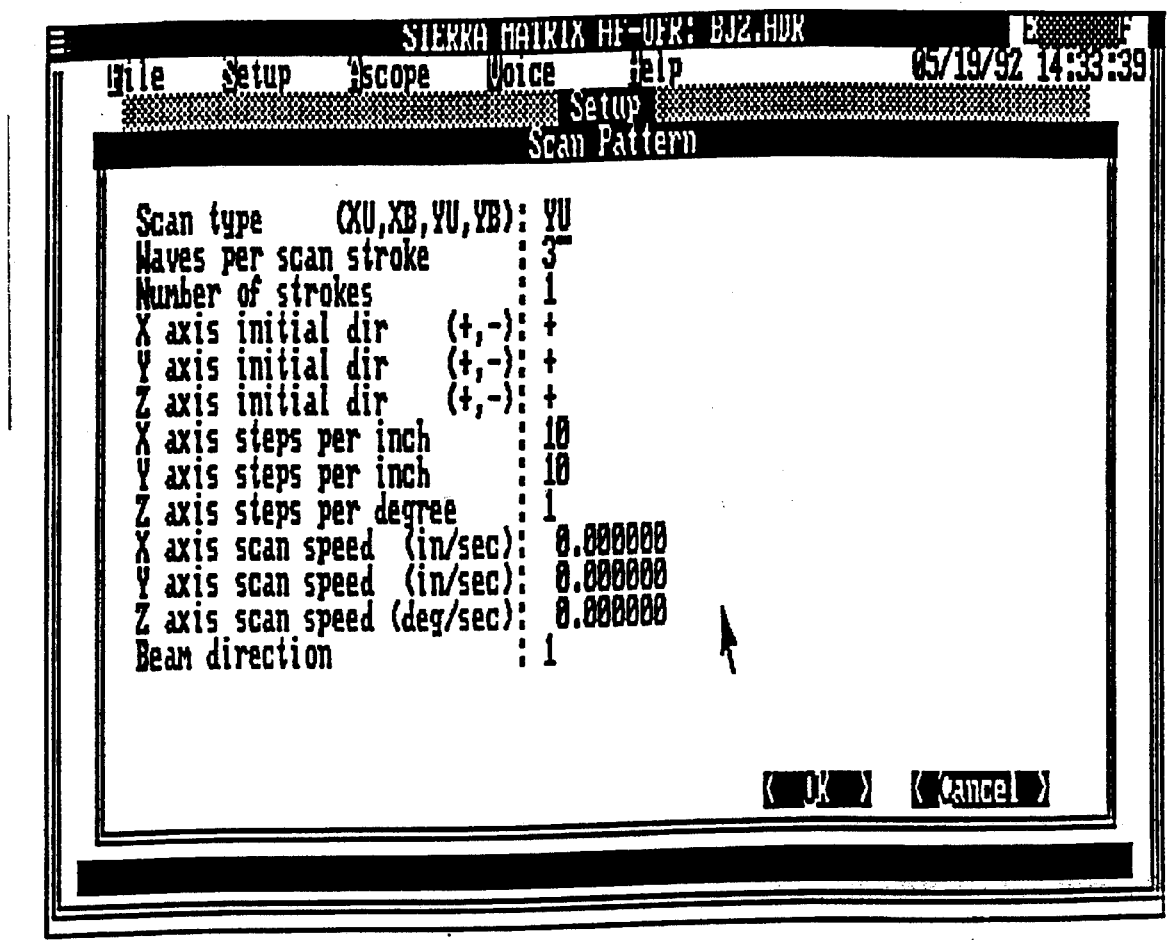
FIG. 12 is a set-up menu of the present invention for the scan pattern description.
Figure 13:
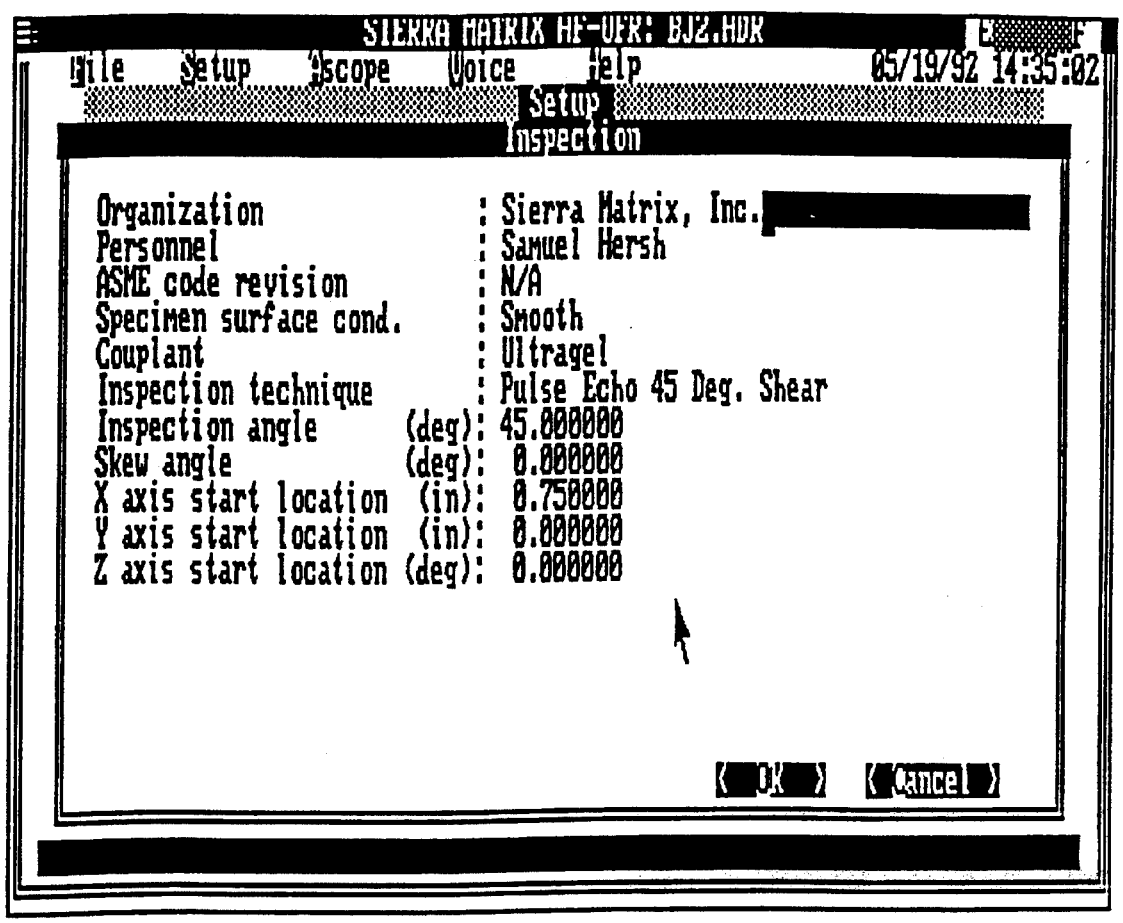
FIG. 13 is a set-up menu of the present invention for the inspection description.
Figure 14:
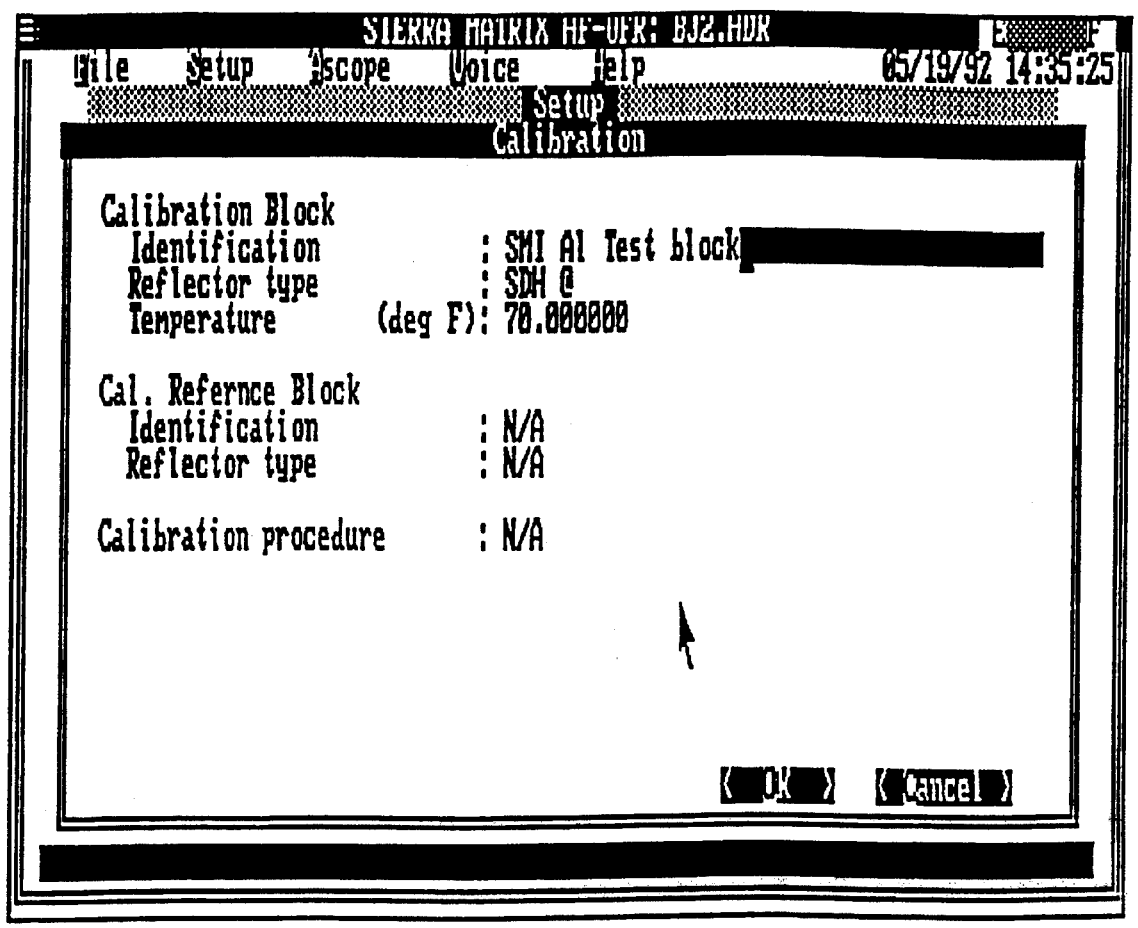
FIG. 14 is a set-up menu of the present invention for the calibration description.
Figure 15:
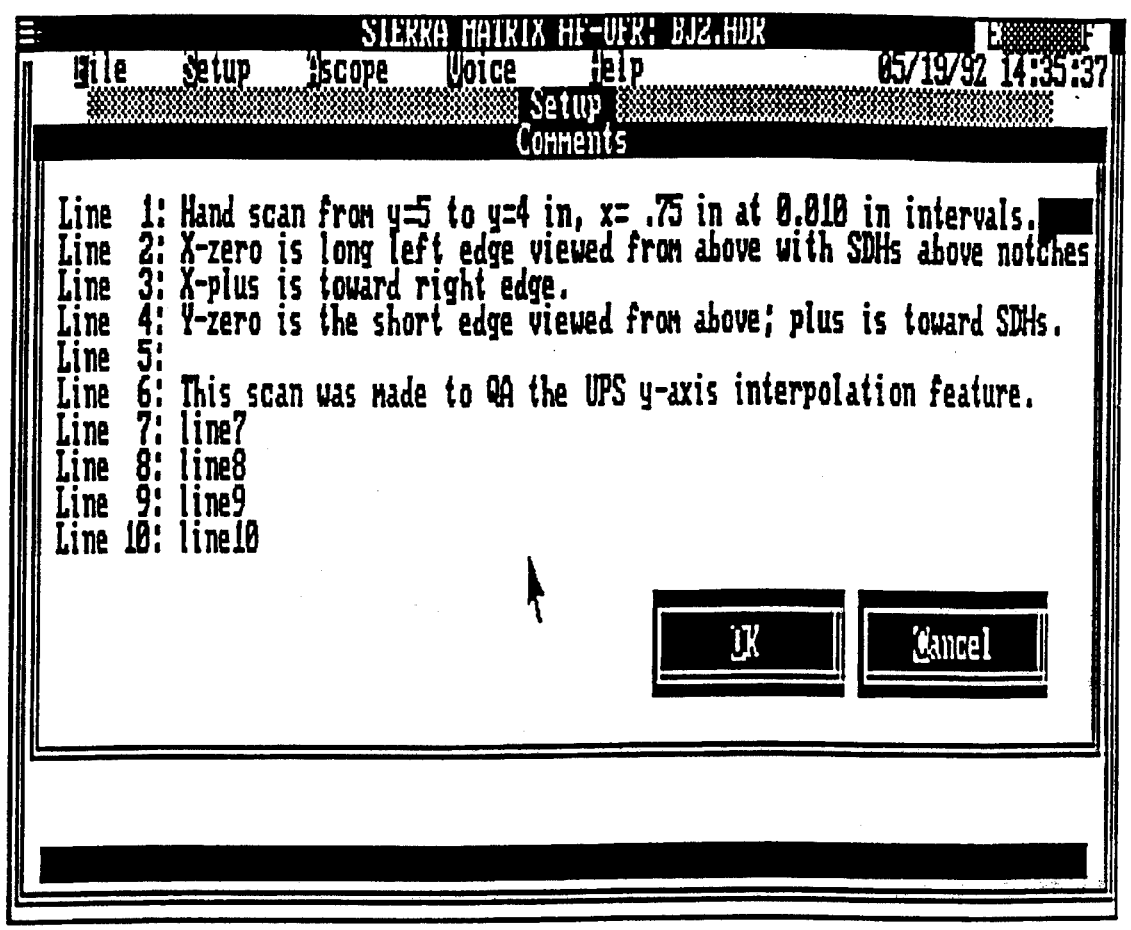
FIG. 15 is a set-up menu of the present invention for the set-up comments.

FIGS. 6a and 6b each show the area of uncertainty 130 for freehand and ruled scans, respectively, for two-axis fully encoded scanners. In order to make the freehand scan efficient, the tolerance region around the target grid point (circled center grid point) is typically set to a relatively large size, in this case about ½ the grid interval, so that the user does not waste a great deal of time trying to accurately strike the grid point. When freehand scanning (FIG. 6a), the target grid point may be approached from any direction 132–138. Because the ruled scan (FIG. 6b) constrains motion in all but one axis, the operator can only approach the grid point from one of two directions 132 and 136, and therefore will intersect the grid point to within the indexing accuracy of the system which is typically quite small.

Menu Tree

Figure 4:
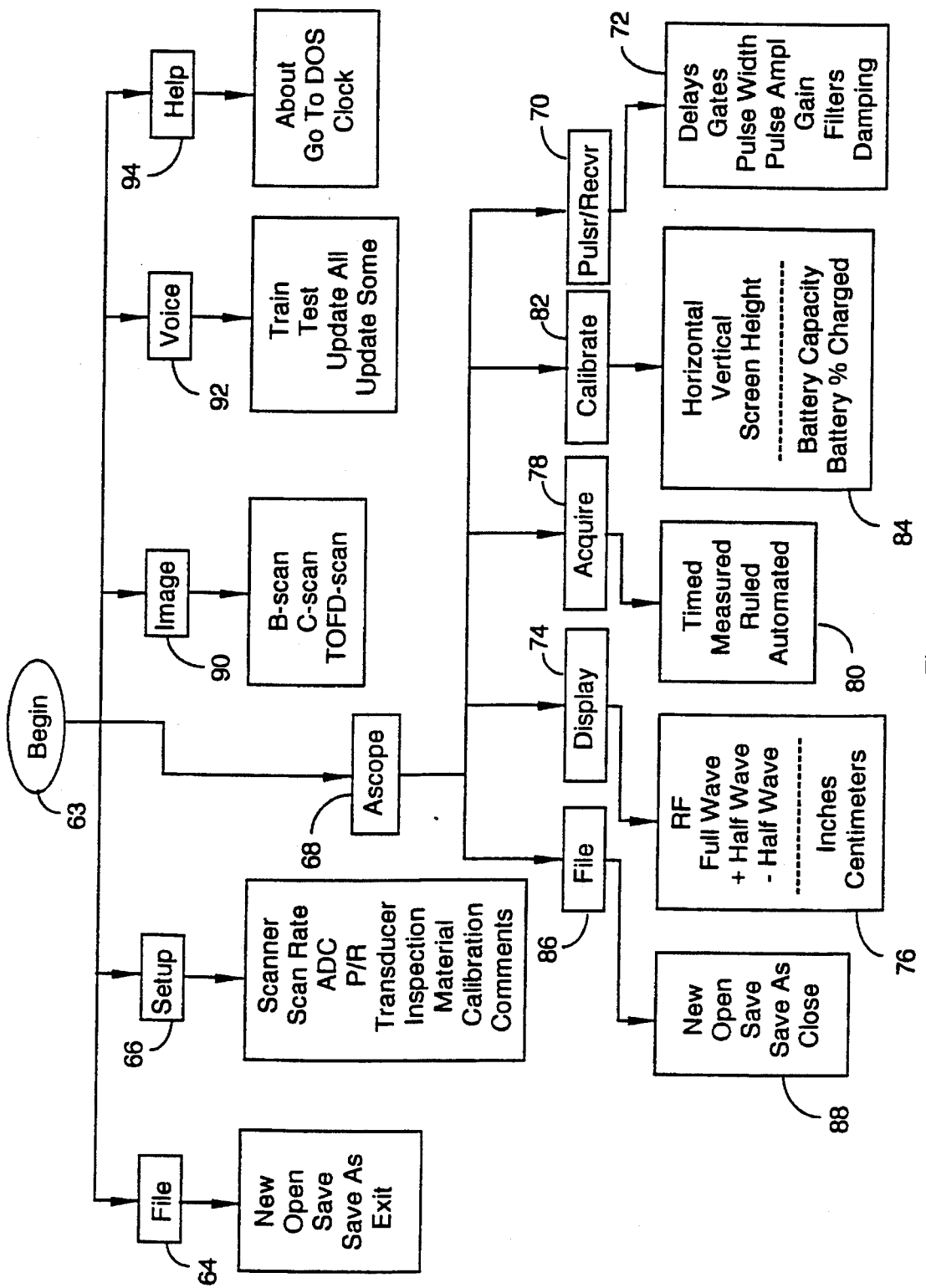
FIG. 4 is a block diagram menu tree of the present invention.

The present invention uses a menu based system that is hierarchically and compatible with the Common User Access (CUA) component of IBM's System Application Architecture (SAA). The menu tree is shown in FIG. 4.

Program Flow

At power on (block 63), the system performs subsystem diagnostics automatically and reports the results of the diagnostic tests on display 32. For example, the basic system CPU, memory and 1/0 functions are tested and the results of each test are reported as either passed or failed. The system settings are initialized to their power-up default values, which are appropriate for ultrasonic testing of a 1-inch thick aluminum block using a 45-degree 2.25 MHz pulse-echo transducer. FIGS. 7–14 show the computer displays associated with the default system settings for various components of the system. For example, the parameters for sound velocity, data acquisition time gate, system gain, filters, wedge delay (time-of-flight in the Lucite wedge coupling the transducer to the test material), pulse width and pulse amplitude are all part of the system power up settings.

File (block 64):

At this point, the user can verify that the system is operational using the default settings on a standard aluminum block or the user can load an existing (pre-stored) setup file by selecting (F)ile (O)pen an selecting a specific setup file or create a new setup file to change the system settings from their power-on default values.

Setup (block 66):

The Setup menu parses the settings into several logical groups, each of which may be viewed on the display 32 and revised as necessary. Sample printouts of these settings are shown in FIGS. 7–14.

Figure 5:
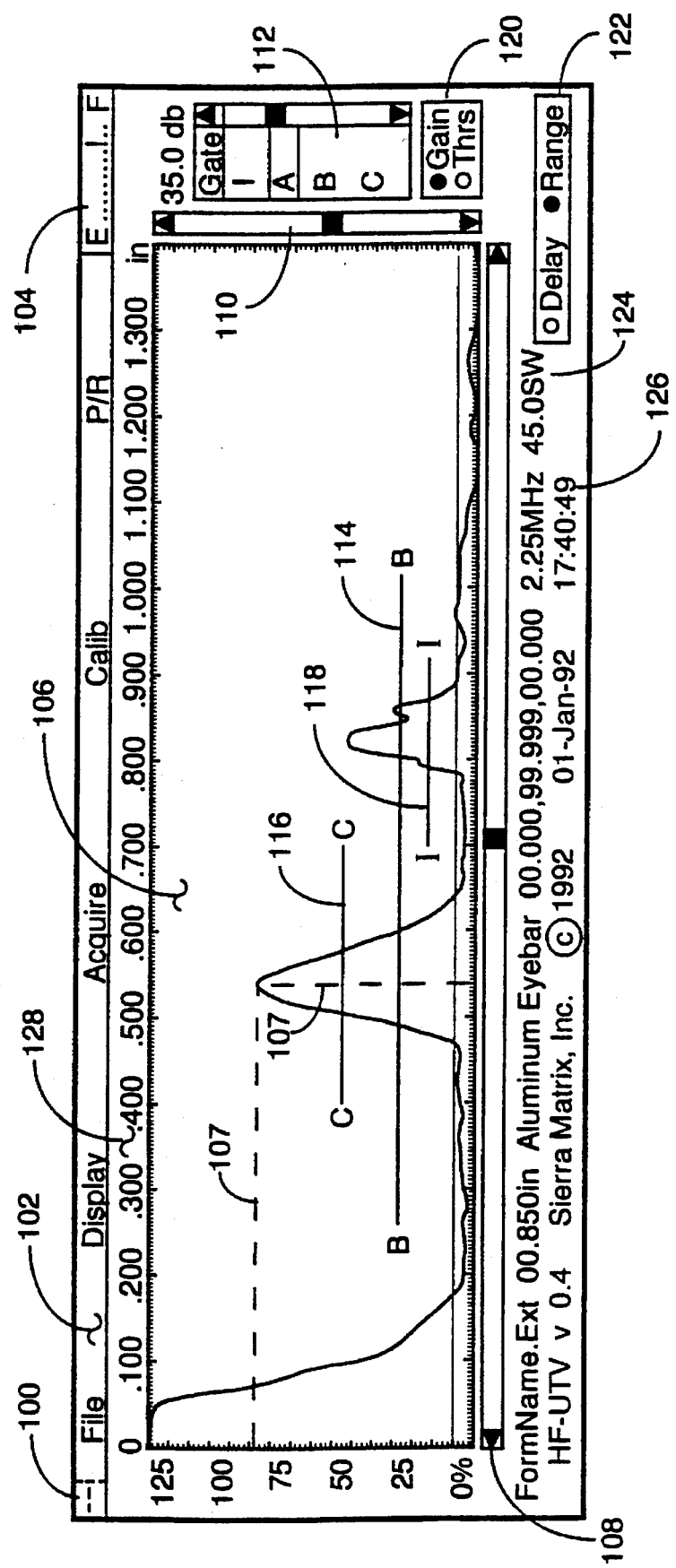
FIG. 5 is a sample A-scope display of the present invention.

Ascope (block 68):

The system settings ay also be adjusted by selecting the A-scope menu. A sample A-scope display is shown in FIG. 5 with the display divided into the following parts:

Top left icon:
  close application icon 100.

Top center area:
  menu bar 102.

Top right area:
  battery power gauge (resembles an auto fuel gauge) 104.

Center area:
  A-scan window 106 which displays a plot of signal amplitude (vertical axis) as a function of time-of-flight (round-trip time from the initial ultrasonic pulse to the return of the pulse echo) or equivalent distance into the test material. The dashed lines 107 indicates the position of a waveform cursor that can be used to obtain the amplitude and time (or distance) to any point on the waveform.

Region immediately below the A-scan window 106:
  the horizontal scroll bar 108 is used to indicate time or distance parameters such as the gate delay and range.

Region immediately to right of A-scan window 106:
  the vertical scroll bar 110 is used to indicate gain or threshold parameters.

Window to right of vertical scroll bar 110:
  the gate window 112 is used to select the current gate, namely, the (I)nterface gate, (A)-scan gate, (B)-scan gate, (C)-scan gate. These are independent gates that permit the operator to gate the region of interest for each type of scan along the time dimension. These gates are shown as labeled horizontal lines 114–118 in the A-scan window 106. The gate start and stop times are given by the line endpoints and a threshold level associated with each gate are given by the gate height in the vertical display dimension. Normally, the gates are referenced to the initial pulse (t=0). However, it may be desirable to use a signal dependent gate, the Interface gate, as a time base reference for the other gates. For example, one may wish to reference the gate to the ultrasonic reflection off the back wall of the part.

Below the gate window 112:
    the gain/threshold radio buttons 120. These are mutually exclusive controls that condition the meaning of the vertical scroll bar 110, namely, whether it controls the system gain or a threshold level associated with the current gate 112.

Below the gain/threshold window 120:
    the delay/range radio buttons 122. These mutually exclusive radio buttons condition the meaning of the horizontal scroll bar 108, namely, whether it controls the gate delay or gate range.

The horizontal line of text 124 immediately below the horizontal scroll bar 108:
    a subset of several useful parameters extracted from the setup file is displayed with the A-scan display.

The horizontal line 126 along the bottom edge: information that identifies the system pedigree, current date and time.

Referring again to FIG. 4, when the A-scope (block 68) menu is selected the system initially operates as a simple flaw detector. In this mode, he A-scan display is generated by first displaying a frame, axes notations and a graticule. Then pulser-receiver 18 and analog-o-digital converter 18 are initialized using the setup information (block 68).

Then the system begins a loop that continues until the user requests a pause or leaves A-scope. The loop consists of (blocks 70–72) firing the pulser section of pulser/receiver 16 and synchronously digitizing the ultrasonic return signal that is amplified and filtered by the receiver section of pulser/receiver 16. The waveform is transferred by microcomputer 12 from the high speed memory of ADC 18 to the system memory of microcomputer 12. The RF waveform may then be processed (blocks 74–76) for positive half-wave, negative half-wave or full-wave rectified display format and transformed to display raster addresses for writing to the display 32. The RF waveform is the raw digitized waveform with both positive and negative excursions about 0 volts. Positive half-wave rectification is performed by assigning all samples with negative amplitudes to 0 volts. Negative half-wave rectification is performed by assigning all samples with positive values to 0 volts and reversing the sign of all negative samples. Full wave rectification is performed by reversing the sign of all negative samples.

Waveforms are written to the buffer of display control 22 using a two-step process to create each pixel. In the first step, the nth sample of the previous waveform is erased using an exclusive-OR (XOR) write; in the second step the nth sample of current waveform is written to the display using an XOR write. This process is repeated for each sample in the waveform, sample by sample until the entire waveform is displayed. If the user has selected one of the data acquisition modes (timed, measured, ruled and automatic are supported by the experimental implementation of the present invention) (blocks 78–80), the waveform may be stored to removable magnetic memory 20.

Then any user input is processed (blocks 82–84); for example, the user may change gates, thresholds, display mode, pulse polarity, pulse width, pulse amplitude, receiver gain, filters or damping. This loop repeats, until the user freezes the current display for analysis or exits the A-scope program altogether.

One pair of radio (mutually exclusive) buttons, DELAY/RANGE 122, are used to define the operation of the horizontal scroll bar 108. If DELAY is selected, then the horizontal scroll bar 108 is used to set the start of a gate. If RANGE is selected, the horizontal scroll bar 108 sets the range (width) of a gate. Similarly, another pair of radio buttons, GAIN/THRS 120, are used to define the operation of the vertical scroll bar 110. If GAIN is selected, the vertical scroll bar is used to set the receiver gain/attenuation. If THRS is selected, the vertical scroll bar 110 sets a threshold value for other processes. The type of gate that is under control is selected in the gate window 112, The gate types as indicated above with relation to FIG. 5 are Interface, A-scan, B-scan and C-scan. A, B and C-scan gates have their normal ultrasonic meanings. The gain, threshold and gate values are updated and displayed to provide immediate operator feedback. Information that identifies the setup file name and some basic setting information is displayed below the waveform information. An estimate of the battery capacity is shown as a gauge in the upper right corner of the A-scope display.

A calibration menu 102 (see FIG. 5) is provided to facilitate ASME standard calibration measurements for ultrasonic instruments. These are a series of measurements that estimate the amplitude (vertical), timebase (horizontal) and display (screen height) linearity. Calibration menu 102 also accepts input from the user about the battery capacity to properly initialize the battery gauge 104.

Image (block 90):

The system image menu supports the display of color or half-tone B-scan, C-scan and Time-of-Flight Diffraction images. These images can be generated from position-encoded or position-implied (measured or timed) RF waveforms. The resulting images may be stored in a standard image format, namely, TIFF or PCX for display on an off-line computer with higher graphics resolution or on a printer. TIFF stands for Tagged Image File Format and PCX is the name of a popular IBM PC compatible image file format used by a program called PC Paintbrush. The user may transfer one or more digitized photographs from the digital camera to the system for permanent storage. These photographs are automatically numbered and cross-referenced to the current setup for consistent and unambiguous documentation of the inspection.

The voice menu (block 92) supports training the speaker-dependent voice recognition algorithm (third-party software). The algorithm is trained by repeating each of the command words until the classification algorithm performance is acceptable. A test feature is provided to test the recognition performance to determine if further training is needed. The voice training may be performed on all of the command vocabulary each pass or on selective commands only.

A help menu (block 94) is used to provide basic information "About" the program name, version and date. The user can also temporarily leave the HF-UTV program and go to DOS to perform system maintenance functions and return where leaving off. The date and time display may be enabled or disabled from this menu.

From the forgoing description, it will be apparent that the invention disclosed herein provides a novel and advantageous system and method for hands-free ultrasonic testing of materials, particularly portions of structures in hard to reach areas. It will be understood by those familiar with the art that the invention may be embodied in other specific forms without departing from the spirit or essential characteristics thereof. Therefore, the scope of protection for the present invention is only limited by the scope of the appended claims.

What is claimed:

1. An ultrasonic test view system for performing non-destructive testing of a specimen of engineered materials and structures under control of a single user operator at a test site comprising:

a scanner under control of said single user operator to transmit ultrasonic signals to, and to detect returning ultrasonic signals from, a selected area of said specimen;

a processor under control of said single user operator coupled to said scanner to control said system and to process said returning signals detected by said scanner to produce a resultant scanned response signal; and a hands-free display under control of said single user operator coupled to said processor to display an image of said resultant scanned response signal, said display being mountable in front of an eye of said single user operator of said system to permit simultaneous viewing of said specimen and said image of said resultant scanned response signal by said single user operator.

2. An ultrasonic test view system as in claim 1 wherein said display projects said image of said resultant scanned response signal onto the retina of said an eye of said single user operator simultaneously with said single user operator viewing the selected area of the specimen being inspected to mentally create a view of the selected area being inspected with the image of the resultant scanned response signal superimposed thereon creating a composite visual display that appears to the single user operator as though the displayed image of the resultant scanned response signal is a transparent overlay on the selected area being inspected.

3. An ultrasonic test view system as in claim 1 wherein said display projects said image of said resultant scanned response signal onto the retina of said an eye of the single user operator simultaneously with said single user operator viewing the selected area of the specimen being inspected to mentally create adjacent views of the selected area being inspected and the image of the resultant scanned response signal creating a composite visual display.

4. A method for simultaneously viewing of a specimen which is being scanned and the resultant scanned response from that specimen by a human user, said method comprising the steps of:

a. viewing said specimen being scanned with an eye of said user; and b. projecting said resultant scanned response onto the retina of an eye of the user for producing a mental picture of said specimen with said resultant scanned response.

5. A method for simultaneously viewing of a specimen as in claim 4 wherein in step b. said mental picture is of said specimen adjacent said resultant scanned response.

6. A method for simultaneously viewing of a specimen as in claim 4 wherein in step b. said mental picture is of said specimen overlaying said resultant scanned response.

* * * * *